United States Patent
Simonet et al.

(10) Patent No.: US 8,642,020 B2
(45) Date of Patent: Feb. 4, 2014

(54) OXIDIZING AQUEOUS DISPERSION FOR TREATING KERATIN FIBERS COMPRISING AT LEAST ONE NONIONIC AMPHIPHILIC HYDROPHOBIC COMPOUND

(75) Inventors: Frédéric Simonet, Touqin (FR); Luc Nicolas-Morgantini, Rully (FR)

(73) Assignee: L'Oreal, Paris (FR)

( * ) Notice: Subject to any disclaimer, the term of this patent is extended or adjusted under 35 U.S.C. 154(b) by 468 days.

(21) Appl. No.: 12/410,682

(22) Filed: Mar. 25, 2009

(65) Prior Publication Data

US 2009/0246160 A1   Oct. 1, 2009

Related U.S. Application Data

(60) Provisional application No. 61/071,180, filed on Apr. 16, 2008.

(51) Int. Cl.
  *A61Q 5/08* (2006.01)
  *A61Q 5/00* (2006.01)

(52) U.S. Cl.
  USPC .... 424/62; 424/70.19; 424/70.21; 424/70.27; 424/70.31

(58) Field of Classification Search
  None
  See application file for complete search history.

(56) References Cited

U.S. PATENT DOCUMENTS

| | | |
|---|---|---|
| 7,160,334 B2 | 1/2007 | Noecker et al. |
| 2001/0023515 A1 | 9/2001 | Cottard et al. |
| 2006/0117498 A1 * | 6/2006 | Bureiko et al. ............ 8/406 |
| 2008/0010754 A1 | 1/2008 | Bureiko et al. |

FOREIGN PATENT DOCUMENTS

| | | |
|---|---|---|
| EP | 0204116 A1 * | 2/1984 |
| FR | 2 803 197 A1 | 7/2001 |

OTHER PUBLICATIONS

French Search Report for FR 0852036, dated Jan. 12, 2009.

* cited by examiner

*Primary Examiner* — Jyothsna Venkat
(74) *Attorney, Agent, or Firm* — Obrien Jones, PLLC

(57) ABSTRACT

The subject of the present disclosure is a composition for treating keratin fibers comprising, in a cosmetically acceptable medium, at least one oxidizing agent; at least one nonionic amphiphilic hydrophobic compound which is solid at ambient temperature; and, optionally, at least one hydrophilic surfactant; wherein the weight ratio of the at least one hydrophilic surfactant to the at least one nonionic amphiphilic hydrophobic compound ranges from 0:1 to 0.16:1, on the condition that when the at least one hydrophilic surfactant is present, it must be chosen from cationic and zwitterionic hydrophilic surfactants; and further wherein the composition is in the form of an aqueous dispersion.

11 Claims, No Drawings

OXIDIZING AQUEOUS DISPERSION FOR TREATING KERATIN FIBERS COMPRISING AT LEAST ONE NONIONIC AMPHIPHILIC HYDROPHOBIC COMPOUND

This application claims benefit of U.S. Provisional Application No. 61/071,180, filed Apr. 16, 2008, the contents of which are incorporated herein by reference. This application also claims benefit of priority under 35 U.S.C. §119 to French Patent Application No. FR 0852036, filed Mar. 28, 2008, the contents of which are also incorporated herein by reference.

The present disclosure relates to a composition for treating keratin fibers, and for example human keratin fibers such as the hair, in the form of an aqueous dispersion comprising, in a cosmetically acceptable medium, at least one oxidizing agent; at least one nonionic amphiphilic hydrophobic compound which is solid at ambient temperature; and, optionally, at least one hydrophilic surfactant; wherein the weight ratio of the at least one hydrophilic surfactant to the at least one nonionic amphiphilic hydrophobic compound ranges from 0:1 to 0.16:1, on the condition that when the at least one hydrophilic surfactant is present, it must be chosen from cationic and zwitterionic hydrophilic surfactants.

In cosmetics, in the fields of the dyeing, bleaching, and permanent reshaping of keratin fibers, and for example human keratin fibers such as the hair, oxidizing compositions are used.

Thus, in oxidation dyeing of the hair, oxidizing compositions are mixed with oxidation dyes (bases and couplers), which are colorless by themselves, in order to generate colored and coloring compounds via a process of oxidative condensation. Oxidizing compositions are also used in direct hair dyeing as a mixture with certain direct dyes which are colored and coloring, in order to obtain a coloration with a hair-lightening effect. Among the oxidizing agents conventionally used for dyeing keratin fibers, mention may be made of hydrogen peroxide or compounds capable of producing hydrogen peroxide by hydrolysis, such as urea peroxide or persalts such as perborates and persulfates, hydrogen peroxide being frequently used.

In hair bleaching, the bleaching compositions contain at least one oxidizing agent. Among these oxidizing agents, those most conventionally used are hydrogen peroxide or compounds capable of producing hydrogen peroxide by hydrolysis, such as urea peroxide or persalts such as perborates, percarbonates, and persulfates, hydrogen peroxide and persulfates being frequently used.

These compositions may be aqueous compositions containing alkaline agents (amines or aqueous ammonia) which are diluted, at the time of use, with an aqueous hydrogen peroxide composition.

These compositions may also be formed from anhydrous products which contain alkaline compounds (alkaline silicates and amines), and a peroxygenated reagent such as ammonium or alkali metal persulfates, perborates or percarbonates, which are diluted, at the time of use, with an aqueous hydrogen peroxide composition.

In permanent hair reshaping, in a first step, the —S—S— disulphide bonds present in keratin (cysteine) are opened using a composition containing a suitable reducing agent (reduction step), and then, after having rinsed the head of hair thus treated, the disulphide bonds are reconstituted, in a second step, by applying, to the hair, which has been placed under tension beforehand (with rollers and the like), an oxidizing composition (oxidation step, also known as fixing step) so as to finally give the hair the desired shape. This technique thus equally makes it possible either to make the hair wavy, or to straighten it or smooth it out. The new shape imposed on the hair with a chemical treatment as discussed above can be lasting and may be able to withstand, for example, the action of washing with water or shampoos, as opposed to the simple conventional techniques of temporary reshaping, such as hairsetting.

The oxidizing compositions used for implementing the fixing step are most commonly compositions based on aqueous hydrogen peroxide.

Most of the current supports used for the oxidizing compositions are formulated using crystallizable compounds, for instance cetylstearyl alcohol. These compounds are generally melted, introduced into the aqueous phase and emulsified under hot conditions. The emulsion is then cooled, causing these compounds to crystallize in the form of solid particles of micrometric size (crystals). Surfactants, for instance highly oxyethylenated (approximately 20 to 30 oxyethylene units) nonionic surfactants, are systematically introduced into the formulations in such a way as to perform the emulsification step. The role of said surfactants is to refine the emulsion and to produce, in the end, a smooth and creamy dispersion free of lumps.

It is found, in general, that this type of support can change during storage. A change in the microscopic appearance can then be noted, with the appearance of new crystal morphologies, in larger clumps. The rheological properties such as viscosity, threshold stress or viscoelastic moduli, may also change, becoming higher or lower.

The compositions disclosed herein provide new oxidizing compositions which do not exhibit at least one of the drawbacks described above, for example oxidizing compositions which can be stable overtime.

Accordingly, one aspect of the present disclosure is a composition for treating keratin fibers comprising, in a cosmetically acceptable medium:

at least one oxidizing agent;

at least one nonionic amphiphilic hydrophobic compound which is solid at ambient temperature; and optionally, at least one hydrophilic surfactant;

wherein the weight ratio of the at least one hydrophilic surfactant to the at least one nonionic amphiphilic hydrophobic compound ranges from 0:1 to 0.16:1;

on the condition that when the at least one hydrophilic surfactant is present, it must be chosen from cationic and zwitterionic hydrophilic surfactants;

and further wherein the composition is in the form of an aqueous dispersion.

The at least one nonionic amphiphilic hydrophobic compound can readily be emulsified under hot conditions in water, like fatty alcohol/highly oxyethylenated nonionic surfactant mixtures. Without being bound by theory, it is believed that the heating results in a state of equilibrium reached as soon as production comes to an end: no reorganization takes place between the various molecules which constitute the crystals.

Consequently, in addition to its simplicity, the composition in accordance with the disclosure can be more stable during storage. For instance, no notable variations are observed in the microscopic appearance or in the rheological properties over time. It may be in the form of a cream with, for example, a shiny appearance and which is very easy to spread over the head of hair or to mix with other media (oxidation dyeing creams, bleaching pastes, etc.).

Thus, the dyeing, bleaching, or permanent reshaping compositions obtained using the oxidizing composition according to the disclosure can be stable and can have improved and more effective application and use qualities.

When the composition according to the disclosure is used for dyeing keratin fibers, good dyeing properties can be obtained, such as powerful, chromatic, sparingly selective colorings which may be color-fast with respect to the various attacks that the hair may be subjected to, such as shampoos, light, sweat, and permanent reshaping.

When the composition in accordance with the present disclosure is used for bleaching keratin fibers, it can make it possible to obtain a good lightening effect on these fibers without damaging them and without impairing their cosmetic properties.

When the composition in accordance with the present disclosure is used for permanently reshaping keratin fibers, it can make it possible to obtain satisfactory permanent reshaping of these fibers without damaging them and without impairing their cosmetic properties.

Another aspect of the present disclosure is a process for treating keratin fibers, such as a process for dyeing, bleaching, or permanently reshaping keratin fibers, comprising applying to the keratin fibers a composition for treating keratin fibers comprising, in a cosmetically acceptable medium:
  at least one oxidizing agent;
  at least one nonionic amphiphilic hydrophobic compound which is solid at ambient temperature; and
  optionally, at least one hydrophilic surfactant;
  wherein the weight ratio of the at least one hydrophilic surfactant to the at least one nonionic amphiphilic hydrophobic compound ranges from 0:1 to 0.16:1;
  on the condition that when the at least one hydrophilic surfactant is present, it must be chosen from cationic and zwitterionic hydrophilic surfactants;
  and wherein the composition for treating keratin fibers is in the form of an aqueous dispersion.

Another aspect of the present disclosure is a method for making a stable cosmetic composition for treating keratin fibers comprising introducing into a cosmetic composition, a composition comprising in a cosmetically acceptable medium:
  at least one oxidizing agent;
  at least one nonionic amphiphilic hydrophobic compound which is solid at ambient temperature; and
  optionally, at least one hydrophilic surfactant;
  wherein the weight ratio of the at least one hydrophilic surfactant to the at least one nonionic amphiphilic hydrophobic compound ranges from 0:1 to 0.16:1;
  on the condition that when the at least one hydrophilic surfactant is present, it must be chosen from cationic and zwitterionic hydrophilic surfactants;
  and wherein the composition is in the form of an aqueous dispersion.

In the subsequent text, unless otherwise indicated, the limits of the ranges indicated are included in the disclosure.

For the purpose of the present disclosure, the term "dispersion" is intended to mean a suspension of solid particles in a liquid.

The composition in accordance with the disclosure is readily emulsified, for example under hot conditions using conventional methods for stirring such as rotor/stator turbines, and is then cooled to ambient temperature so as to form the solid particles.

For the purpose of the present disclosure, the term "ambient temperature" is intended to mean a temperature of 25° C. plus or minus 5° C.

The at least one oxidizing agent present in the composition in accordance with the disclosure is chosen from hydrogen peroxide, urea peroxide, alkali bromates, polythionates and persalts, such as perborates, percarbonates, and persulfates.

For example, in at least one embodiment, the at least one oxidizing agent is chosen from hydrogen peroxide and bromates.

The at least one oxidizing agent is present in an amount ranging from 0.1% to 50% by weight, for example from 1% to 20% by weight, relative to the total weight of the oxidizing composition.

According to at least one embodiment of the present disclosure, when the at least one oxidizing agent is hydrogen peroxide, the oxidizing composition further comprises at least one agent for stabilizing aqueous hydrogen peroxide.

By way of examples of agents for stabilizing aqueous hydrogen peroxide, mention may be made of alkali metal or alkaline-earth metal pyrophosphates such as tetrasodium pyrophosphate, alkali metal or alkaline earth metal stannates, phenacetin or oxyquinoline acid salts such as oxyquinoline sulfate. For example, at least one stannate may be used, possibly in combination with at least one pyrophosphate.

The at least one agent for stabilizing aqueous hydrogen peroxide may be present in an amount ranging from 0.0001% to 5% by weight, for example from 0.01% to 2% by weight, relative to the total weight of the oxidizing composition.

In the context of the present disclosure, the term "amphiphilic compounds" is intended to mean water-dispersible compounds having at least one polar part and at least one apolar part.

In at least one embodiment of the disclosure, the at least one nonionic amphiphilic hydrophobic compound comprises at least one $C_{12}$-$C_{30}$ saturated fatty chain linked, via an ether, ester, amide or carbamate bond, to a polar head composed of at least one unit chosen from oxyalkylene units, sorbitan units, sugar units, and other polyol units.

By way of examples of oxyalkylene units, mention may be made of oxyethylene and oxypropylene units.

By way of examples of sugar units, mention may be made of glucose and fructose units.

By way of examples of other polyol units, mention may be made of glycerol, tetritol, pentitol, sorbitol, mannitol, and hexitol units.

The expression "nonionic amphiphilic hydrophobic compound" is intended to mean, for the purpose of the present disclosure, any nonionic amphiphilic compound which, at ambient temperature, has a water-solubility of less than 2%, such as less than 1%.

According to at least one embodiment of the present disclosure, the at least one nonionic amphiphilic hydrophobic compound has a calculated HLB ranging from 2 to 10. The calculated HLB is defined as being the following coefficient.

$$HLB = 20 \times \text{molar mass of the hydrophilic part/total molar mass}$$

For an oxyethylenated fatty alcohol, the hydrophilic part corresponds to the oxyethylene units condensed with the fatty alcohol, and the calculated HLB then corresponds to the HLB according to Griffin (Griffin W. C., J. Soc. Cosmet. Chemists, 5, 249, 1954). For an ester or an amide, the hydrophilic part is naturally defined as being beyond the carbonyl group, starting from the fatty chain(s). Of course, this figure is additive and for a mixture of molecules, the calculated HLB corresponds to the weighted mean by mass of the calculated HLBs for each molecule.

The at least one nonionic amphiphilic hydrophobic compound has a sufficiently high melting point to be capable of forming, in water, solid particles at ambient temperature.

According to at least one embodiment of the present disclosure, the melting point of the at least one nonionic amphiphilic hydrophobic compound is greater than 30° C., and for example greater than 40° C.

By way of examples of nonionic hydrophobic compounds which can be used in the present disclosure, mention may be made of the following compounds:

| INCI name | Commercial reference | Calculated HLB |
|---|---|---|
| Steareth-2 | BRIJ 72 (Uniqema) | 4.9* |
| Steareth-3 | ISOXAL 5 (Vevy) | 6.6* |
| Steareth-4 | NIKKOL BS-4 (Nikko) | 7.9* |
| Steareth-5 | JEECOL SA-5 (Jeen) | 9.0* |
| Steareth-6 | EMALEX 606 (Nihon Emulsion) | 9.9* |
| Ceteth-2 | BRIJ 52 (Uniqema) | 5.3* |
| Ceteth-3 | EMALEX 103 (Nihon Emulsion) | 7.1* |
| Ceteth-4 | LIPOCOL C-4 (Lipo) | 8.4* |
| Ceteth-5 | VOLPO C5 (Croda) | 9.5* |
| Cetearteth-2 | VOLPO CS2 (Croda) | 5.1* |
| Cetearteth-3 | JEECOL CS-3 (Jeen) | 6.8* |
| Cetearteth-4 | LIPOCOL SC-4 (Lipo) | 8.1* |
| Cetearteth-5 | VOLPO CS5 (Croda) | 9.2* |
| Beheneth-5 | NIKKOL BB-5 (Nikko) | 8.1* |
| Cocamide MEA | COMPERLAN 100 (Cognis) | 4.8 |
| Cocamide MIPA | NINOL M-10 (Stepan) | 5.6 |
| Cocamide DEA | COMPERLAN KD (Cognis) | 7.1 |
| Stearamide MEA | MONAMID S (Uniqema) | 3.7 |
| Stearamide DEA | LIPAMIDE S (Lipo) | 5.6 |
| Myristamide DEA | JEEMIDE MRCA (Jeen) | 6.6 |
| Myristamide MEA | WITCAMIDE MM (Witco) | 4.4 |
| Polyglyceryl-2 distearate | EMALEX DSG-2 (Ikeda) | 4.7 |
| Polyglyceryl-3 distearate | CITHROL 2623 (Croda) | 6.2 |
| Polyglyceryl-2 stearate | NIKKOL DGMS (Nikko) | 7.6 |
| Polyglyceryl-3 stearate | RADIASURF 7248 (Atofina) | 9.4 |
| Peg-2 stearate | SEDEFOS 75 (Gattefosse) | 5.6 |
| Peg-3 stearate | TEGIN D 1102 (Goldschmidt) | 7.2 |
| Peg-4 stearate | CITHROL 2MS (Croda) | 8.4 |
| Sorbitan distearate | SORBON S-66 (Toho) | 4.7 |
| Sorbitan palmitate | SPAN 40 (Uniqema) | 8.1 |
| Sorbitan stearate | SPAN 60 (Uniqema) | 7.6 |
| Sorbitan tristearate | SPAN 65 (Uniqema) | 3.3 |
| Myristyl glucoside | MONTANOV 14 (Seppic) | 9.5 |
| Cetearyl glucoside | TEGO CARE CG 90 (Degussa) | 8.6 |
| Arachidyl glucoside | MONTANOV 202 (Seppic) | 7.8 |

*corresponding to the HLB calculated according to the Griffin method

The at least one nonionic amphiphilic hydrophobic compound is present in an amount ranging from 2% to 30% by weight, for example from 2% to 20% by weight, such as from 2% to 10% by weight, relative to the total weight of the oxidizing composition.

For the purpose of the present disclosure, the expression "hydrophilic surfactant" is intended to mean surfactants having a calculated HLB of greater than 10, such as ranging from 10 to 50

The at least one hydrophilic surfactant when present as disclosed herein, must be chosen from cationic and zwitterionic hydrophilic surfactants.

The at least one cationic hydrophilic surfactant may be chosen, for example, from mono($C_8$-$C_{30}$)alkyltrimethylammonium salts and quaternary diesters.

The at least one zwitterionic hydrophilic surfactant may be chosen, for example, from alkylbetaines, alkylamidoalkylbetaines, sultaines, phosphobetaines, and amphodiacetates, such as alkylbetaines and amphodiacetates.

In the composition disclosed herein, the weight ratio of the at least one hydrophilic surfactant to the at least one nonionic amphiphilic hydrophobic compound ranges from 0:1 to 0.16:1. For example, this weight ratio can range from 0:1 to 0.10:1, such as from 0:1 to 0.05:1.

According to at least one embodiment of the present disclosure, the composition does not comprise any hydrophilic surfactant.

According to another embodiment of the present disclosure, the composition further comprises at least one $C_{12}$-$C_{30}$ fatty alcohol with a calculated HLB of less than 2.

For example, the at least one fatty alcohol can be chosen from linear and branched, saturated and unsaturated, non-(poly)oxyalkylenated and non-(poly)glycerolated alcohols comprising at least one fatty chain containing from 12 to 30 carbon atoms, for example from 14 to 22 carbon atoms, such as from 16 to 18 carbon atoms, the fatty chains being optionally substituted with one or two additional hydroxyl groups. When the at least one fatty alcohol is unsaturated, it comprises from 1 to 3 carbon-carbon (—C═C—) double bonds, which may or may not be conjugated. For example, the at least one fatty alcohol can be a saturated monoalcohol.

By way of examples of fatty alcohols, mention may be made of lauryl alcohol, cetyl alcohol, stearyl alcohol, behenyl alcohol, myristyl alcohol, linoleyl alcohol, undecylenyl alcohol, palmitoleyl alcohol, linolenyl alcohol, arachidonyl alcohol, erucyl alcohol, isocetyl alcohol, isostearyl alcohol, isobehenyl alcohol, and oleyl alcohol, and mixtures thereof.

For example, in at least one embodiment, the at least one fatty alcohol is chosen from stearyl alcohol, behenyl alcohol, and cetyl alcohol.

The at least one $C_{12}$-$C_{30}$ fatty alcohol can be present in an amount ranging from 0 to 10% by weight, for example from 0 to 2% by weight, such as from 0 to 0.5% by weight, relative to the total weight of the oxidizing composition.

According to at least one embodiment of the present disclosure, the composition does not comprise any $C_{12}$-$C_{30}$ fatty alcohol.

For the purpose of the present disclosure, the term "cosmetically acceptable medium" is intended to mean a medium compatible with keratin fibers, for example human keratin fibers such as the hair.

The cosmetically acceptable medium of the composition in accordance with the present disclosure generally comprises water or a mixture of water and at least one organic solvent. By way of organic solvents, mention may, for example, be made of $C_1$-$C_4$ lower alkanols, such as ethanol and isopropanol; aromatic alcohols such as benzyl alcohol or phenoxyethanol; polyols or polyol ethers, such as ethylene glycol monomethyl, monoethyl and monobutyl ethers, propylene glycol or ethers thereof such as propylene glycol monomethyl ether, butylene glycol, dipropylene glycol and also diethylene glycol alkyl ethers such as diethylene glycol monoethyl ether or monobutyl ether, or else glycerol; and also mixtures thereof.

The at least one solvent can be, for example, present in a total amount ranging from 0.1% to 35% by weight, relative to the total weight of the oxidizing composition, for example from 1% to 40% by weight.

The composition in accordance with the disclosure may also comprise at least one additional compound, or "adjuvant," conventionally used in the cosmetics field. These compounds may for example be chosen from thickening or stabilizing polymers, non-silicone conditioning polymers, silicones, chelating agents, and also fragrances.

Of course, those skilled in the art will take care to select this or these possible additional compound(s) in such a way that the beneficial properties intrinsically associated with the composition in accordance with the disclosure are not, or are not substantially, impaired by the addition(s) envisaged.

The composition according to the disclosure may be in various forms, such as in the form of a cream, a gel, a milk, a lotion, or a mousse, or in any other form suitable for carrying out the treatment of keratin fibers, for example human keratin fibers such as the hair. For instance, in at least one embodiment it is in the form of a cream or a milk.

The pH of the oxidizing composition disclosed herein generally ranges from 1.5 to 4.5, such as from 2 to 3.5. It may be adjusted by adding acidifying agents such as hydrochloric acid, acetic acid, lactic acid, boric acid, citric acid, or phosphoric acid, or acidifying agents in the presence of alkaline agents.

The present disclosure also provides a process for treating keratin fibers, comprising applying to the keratin fibers a composition for treating keratin fibers comprising, in a cosmetically acceptable medium:
at least one oxidizing agent;
at least one nonionic amphiphilic hydrophobic compound which is solid at ambient temperature; and
optionally, at least one hydrophilic surfactant;
wherein the weight ratio of the at least one hydrophilic surfactant to the at least one nonionic amphiphilic hydrophobic compound ranges from 0:1 to 0.16:1;
on the condition that when the at least one hydrophilic surfactant is present, it must be chosen from cationic and zwitterionic hydrophilic surfactants;
and wherein the composition for treating keratin fibers is in the form of an aqueous dispersion.

The oxidizing composition disclosed herein may, for example, be used in a process for dyeing keratin fibers, for example human keratin fibers such as the hair.

The process for dyeing keratin fibers in accordance with the disclosure uses a dye composition comprising, in a support suitable for dyeing keratin fibers, at least one direct dye and/or at least one oxidation dye and at least one oxidizing composition as defined above.

According to this process, the dye composition is applied to the keratin fibers, the color being revealed at acidic, neutral, or alkaline pH using an oxidizing composition according to the disclosure which is applied simultaneously or sequentially, with or without intermediate rinsing.

According to at least one embodiment of the dyeing process disclosed herein, the at least one dye composition is mixed, at the time of use, with at least one oxidizing composition according to the disclosure. The mixture obtained is subsequently applied to the keratin fibers and left on for 3 to 50 minutes approximately, for example 5 to 30 minutes approximately, after which time the fibers are rinsed, washed with shampoo, rinsed again, and dried.

The at least one direct dye may be chosen from the direct dyes conventionally used in direct dyeing. By way of examples, these direct dyes may be chosen from nitrobenzene dyes, azo direct dyes, methine direct dyes, quinone direct dyes, azine direct dyes, triarylmethane direct dyes, indoamine direct dyes, and natural direct dyes. These direct dyes may be nonionic, anionic, or cationic in nature.

Among the benzene direct dyes, mention may be made of 1,4-diamino-2-nitrobenzene, 1-amino-2-nitro-4-(β-hydroxyethylamino)benzene, 1-amino-2-nitro-4-bis(β-hydroxyethyl)aminobenzene, 1,4-bis(β-hydroxyethylamino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(β-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(β-hydroxyethylamino)-4-nitrobenzene, 1-amino-2-[tris(hydroxymethyl)methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitro-benzene, 1-methoxy-2-β-hydroxyethylamino-5-nitro-benzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis(β-hydroxyethyl)amino]-3-nitrobenzene, 1-β-hydroxyethylamino-2-nitrobenzene, and 1-hydroxy-4-β-hydroxyethylamino-3-nitrobenzene.

Among the azo direct dyes, mention may be made of the cationic azo dyes described in Patent Application Publication Nos. WO 95/15144, WO 95/01772, EP 0 714 954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369, and FR 2 844 269.

Among these compounds, further mention may be made of, for example, 1,3-dimethyl-2-[[4-(dimethylamino)phenyl]azo]-1H-imidazolium chloride, 1,3-dimethyl-2-[(4-aminophenyl)azo]-1H-imidazolium chloride, and 1-methyl-4-[(methylphenylhydrazono)-methyl]pyridinium methyl sulfate.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9

Mention may also be made of 1-(4'-aminodiphenylazo)-2-methyl-4-bis(β-hydroxyethyl)aminobenzene, and 4-hydroxy-3-(2-methoxyphenylazo)-1-naphthalenesulphonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, and 1,4-bis(β,γ-dihydroxypropylamino)anthraquinone.

Among the azine dyes, mention may be made of the following compounds: Basic Blue 17, Basic Red 2.

Among the triarylmethane dyes, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes, mention may be made of the following compounds: 2-β-hydroxyethlyamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-(3'-chloro-4'-methylamino)phenylureido-6-methyl-1,4-benzoquinoneimine, and 3-[4'-N-(ethylcarbamylmethyl)amino]phenylureido-6-methyl-1,4-benzoquinoneimine.

Among the natural direct dyes that can be used according to the disclosure, mention may be made of lawsone, juglone, alizarin, purpurin, carminic acid, kermesic acid, purpurogallin, protocatechaldehyde, indigo, isatin, curcumin, spinulosin, apigenidin, and orceins. Use may also be made of extracts or decoctions containing these natural dyes and for example henna-based poultices or extracts.

The at least one direct dye can be present in the dye composition in an amount ranging from 0.001% to 20% by weight, of the total weight of the composition, for example from 0.005% to 10% by weight.

The at least one oxidation dye may be chosen from the oxidation bases and the couplers conventionally used in the dyeing field.

By way of examples of oxidation bases, mention may be made of para-phenylenediamines, double bases, para-aminophenols, ortho-aminophenols, heterocyclic bases, and addition salts thereof.

Among the para-phenylenediamines, mention may be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-β-(4'-aminophenyl)pyrrolidine, and addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and addition salts thereof with an acid, are frequently used.

Among the double bases, mention may be made, by way of example, of bisphenylalkylenediamines and bis-para-aminophenols.

Among the bisphenylalkylenediamines, mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and addition salts thereof with an acid.

Among the para-aminophenols, mention may be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(1-hydroxyethyl-aminomethyl)phenol, 4-amino-2-fluorophenol, and addition salts thereof with an acid.

Among the ortho-aminophenols, mention may be made, by way of example, of 2-aminophenol, 2-amino-5-methylphenol, 2-amino-6-methylphenol, 5-acetamido-2-aminophenol, and addition salts thereof with an acid.

Among the heterocyclic bases, mention may be made, by way of example, of pyridine derivatives, pyrimidine derivatives, and pyrazole derivatives.

Among the pyridine derivatives, mention may be made of the compounds described, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and addition salts thereof with an acid.

Other pyridine oxidation bases that are of use in the present disclosure are the 3-aminopyrazolo[1,5-a]pyridine oxidation bases, or addition salts thereof, described for example in Patent Application Publication No. FR 2801308, By way of example, mention may be made of pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridin-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diamino-pyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)(2-hydroxyethyl)amino]ethanol; 2-[(3-aminopyrazolo[1,5-a]pyridin-7-yl)(2-hydroxyethyl)amino] ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and also addition salts thereof with an acid or with a base.

Among the pyrimidine derivatives, mention may be made of the compounds described, for example, in Patents DE 2359399; JP 88-169571; JP 05-63124; EP 0770375, or Patent Application Publication No. WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in Patent Application Publication No. FR-A-2750048, and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a] pyrimidine, and addition salts thereof with an acid, and the tautomeric forms thereof, when a tautomeric equilibrium exists.

Among the pyrazole derivatives, mention may be made of the compounds described in Patents DE 3843892 and DE 4133957 and Patent Application Publication Nos. WO 94/08969, WO 94/08970, FR-A-2 733 749, and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and addition salts thereof with an acid.

By way of pyrazole derivatives, mention may also be made of diamino-N,N-dihydropyrazopyrazolones, and for instance those described in Application Publication No. FR 2 886 136, such as the following compounds and addition salts thereof.

Among these compounds, mention may be made, for example, of the following:
2,3-diamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
4,5-diamino-1,2-dimethyl-1,2-dihydropyrazol-3-one,
4,5-diamino-1,2-diethyl-1,2-dihydropyrazol-3-one,
4,5-diamino-1,2-di-(2-hydroxyethyl)-1,2-dihydro-pyrazol-3-one,
2-amino-3-(2-hydroxyethyl)amino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2,3-diamino-5,6,7,8-tetrahydro-1H,6H-pyridazino[1,2-a]pyrazol-1-one,
4-amino-1,2-diethyl-5-(pyrrolidin-1-yl)-1,2-dihydro-pyrazol-3-one,
4-amino-5-(3-dimethylaminopyrrolidin-1-yl)-1,2-diethyl-1,2-dihydropyrazol-3-one, and
2,3-diamino-6-hydroxy-6,7-dihydro-1H,5H-pyrazolo[1,2-a]pyrazol-1-one.

As heterocyclic bases, mention may be made, for example, of 4,5-diamino-1-(β-hydroxyethyl)pyrazole, 2,3-diamino-6,7-dihydro-1H,5H-pyrazolo[1,2-a]pyrazol-1-one, and addition salts thereof.

The at least one oxidation base may generally be present in the dye composition in an amount ranging from 0.001% to 10% by weight, of the total weight of the composition, for example from 0.005% to 6% by weight approximately.

By way of examples of couplers, mention may be made of meta-phenylenediamines, meta-aminophenols, meta-diphenols, naphthalene couplers, heterocyclic couplers, and addition salts thereof.

Mention may for example be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and addition salts thereof with an acid.

The at least one coupler may generally be present in the dye composition in an amount ranging from 0.001% to 10% by weight, of the total weight of the composition, for example from 0.005% to 6% by weight.

In general, the at least one oxidation base and at least one coupler addition salts that can be used in the context of the disclosure can be, for instance chosen from the addition salts with an acid, such as hydrochlorides, hydrobromides, sulfates, citrates, succinates, tartrates, lactates, tosylates, benzenesulphonates, phosphates, and acetates, and the addition salts with a base, such as sodium hydroxide, potassium hydroxide, aqueous ammonia, amines, or alkanolamines.

The oxidizing composition according to the disclosure may also be used in a process for bleaching keratin fibers, for example human keratin fibers such as the hair.

The bleaching process according to the disclosure comprises applying to the keratin fibers, a bleaching composition comprising for example aqueous hydrogen peroxide in an alkaline medium after extemporaneous mixing. Conventionally, this is followed by rinsing the keratin fibers.

The bleaching composition applied to the keratin fibers may be obtained by mixing at least one oxidizing composition according to the disclosure with at least one aqueous or anhydrous composition containing for example at least one alkaline agent. The anhydrous composition may be pulverulent or in the form of a paste, and in both cases may contain, for example, at least one peroxygenated salt, such as at least one persulfate. The anhydrous composition in the form of a paste also contains at least one organic inert liquid.

Another aspect of the present disclosure is a process for permanently reshaping keratin fibers, for example human keratin fibers such as the hair, using an oxidizing composition as defined above.

According to this process, a reducing composition is applied to the keratin fibers to be treated, the keratin fibers being placed under mechanical tension before, during, or after the application of the reducing composition, the fibers are optionally rinsed, the oxidizing composition disclosed herein is applied to the optionally rinsed fibers, and then the fibers are optionally rinsed again.

This process begins with applying at least one reducing composition to the hair. This application can be performed lock by lock or to the whole head of hair.

The reducing composition comprises at least one reducing agent, which may be chosen for example from thioglycolic acid, cysteine, cysteamine, glyceryl thioglycolate, and thiolactic acid, or thiolactic acid or thioglycolic acid salts.

The process of placing the hair under tension in a shape corresponding to the final shape desired for the hair (for example curls) may be carried out by any method that is suitable and known per se for keeping the hair under tension, for instance rollers, curlers, combs, and the like.

The hair may also be shaped without the aid of external devices, simply with the fingers.

Before optionally rinsing, it is conventionally appropriate to leave at rest for a few minutes, generally for a period of time ranging from 5 minutes to one hour, for example from 10 to 30 minutes, the head of hair to which the reducing composition has been applied, so as to allow the reducing agent sufficient time to act correctly on the hair. This waiting phase can be, for instance, carried out at a temperature ranging from 35° C. to 45° C., frequently while also protecting the hair with a hood.

In the second optional rinsing, the hair impregnated with the reducing composition is thoroughly rinsed with an aqueous composition.

Next, the oxidizing composition disclosed herein is applied to the hair thus rinsed, with the aim of fixing the new shape given to the hair.

As in the case of the application of the reducing composition, the head of hair to which the oxidizing composition has been applied is then, conventionally, left in a standing or waiting phase that lasts a few minutes, generally a period of time ranging from 3 to 30 minutes, such from 5 to 15 minutes.

If the hair was kept under tension by a device or apparatus, the devices (rollers, curlers and the like) may be removed from the head of hair before or after the fixing.

Finally, the hair impregnated with the oxidizing composition may optionally be rinsed thoroughly, generally with water.

Another aspect of the present disclosure is also the use, for treating keratin fibers, and for example human keratin fibers such as the hair, of an oxidizing composition as defined above.

Still another aspect of the present disclosure is the use, for dyeing keratin fibers, for example human keratin fibers such as the hair, of an oxidizing composition as defined above.

Yet another aspect of the present disclosure is also the use, for bleaching keratin fibers, for example human keratin fibers such as the hair, of an oxidizing composition as defined above.

Another aspect of the present disclosure is also the use, for permanently reshaping keratin fibers, for example human keratin fibers such as the hair, of an oxidizing composition as defined above.

The following examples illustrate the present disclosure without being limiting in nature.

EXAMPLES

The following oxidizing compositions were in the form of smooth and homogeneous creams which changed very little over time, both in terms of the state of the dispersion (microscopic appearance, particle size) and in terms of the rheological parameters:

| Composition | 1 | 2 | 3 | 4 |
|---|---|---|---|---|
| Steareth-2 (Brij 72, Uniqema) | 4 g | — | 5 g | 5 g |
| Beheneth-5 (Nikkol BB-5, Nikko) | — | 4 g | — | — |
| Behenyltrimethyl-ammonium chloride at 79% in a water/isopropanol mixture (Genamin KDMP, Clariant) | — | — | — | 1 g |
| Glycerol | — | — | 1.5 g | 1.5 g |
| Hydrogen peroxide as a 50% aqueous solution | 12 g | 12 g | 4.8 g | 4.8 g |
| Sodium salicylate | 0.035 g | 0.035 g | 0.035 g | 0.035 g |
| Etidronic acid, tetrasodium salt as a 30% aqueous solution | 0.2 g | 0.2 g | 0.2 g | 0.2 g |
| Tetrasodium pyrophosphate•10H$_2$O | 0.04 g | 0.04 g | 0.04 g | 0.04 g |
| Demineralized water | q.s. 100 g | q.s. 100 g | q.s. 100 g | q.s. 100 g |

In addition to their storage stability, their qualities of use were also improved compared with the existing technologies, such as in terms of opacity, of sheen appearance and of rheological behaviour.

Oxidation Dyeing Example

Composition 1 and composition 2 were each mixed with an oxidation dyeing cream (L'Oreal Majirouge® shade 6.64) in weight proportions of 1/1.5 (dyeing cream/oxidizing composition) using a brush and a bowl, and this rapidly resulted in a smooth cream that was easy to apply along the lengths and to the ends of a dry and unwashed head of hair. After a leave-in time of 35 minutes, rinsing, shampooing and then drying, two tones of lightening were obtained, and the result of the dyeing was at least equivalent to that which was obtained with a prior art oxidizing composition having the same oxidizing strength (corresponding to 20 volumes aqueous hydrogen peroxide) and comprising water, hydrogen peroxide, cetylstearyl alcohol, oxyethylenated cetylstearyl alcohol comprising 30 mol of ethylene oxide and $C_{13}/C_{15}$ alkyl ether carboxylic acid monoethanolamide comprising 2 mol of ethylene oxide, but not comprising any nonionic amphiphilic hydrophobic compound that was useful in the context of the disclosure, i.e. the L'Oreal Professionnel 20 Volumes® oxidizing composition 1 (composition A). The head of hair had for example a pleasant feel.

Permanent-Waving Example

The hair was washed, wrung out and rolled on curlers. The Dulcia Tonica® force Cheveux Naturel reducing composition was applied to the entire head of hair and a waiting period of 15 minutes was observed. The head of hair was rinsed. Composition 3 was applied to each curler and a waiting period of 5 minutes was observed. The curlers were removed and Composition 3 was added to the entire head of hair, while massaging the ends. A waiting period of 5 minutes was observed. The head of hair was rinsed and then dried. The head of hair had even curls and a very pleasant feel.

Thiolated Smoothing Example

The hair was washed and wrung out. The X Tenso® force Cheveux Naturel reducing composition was applied, with a brush or by hand, to the entire head of hair and a waiting period of 30 minutes was observed. The head of hair was rinsed. Composition 3 was applied to the entire head of hair and a waiting period of 10 minutes was observed. The head of hair was rinsed. The head of hair had a very smooth appearance and a very pleasant feel.

Identical results were obtained by substituting Composition 3 with Composition 4.

Bleaching Example

Composition 1 and Composition 2 were each mixed with a Platifiz™ Precision bleaching powder in weight proportions of 1/2.5 (bleaching powder/oxidizing composition) in a bowl using a brush, until a smooth cream was obtained. This cream was applied to the entire head of hair using the brush, and then a waiting period of 30 to 50 minutes was observed depending on the desired level of lightening. Next, the head of hair was rinsed and then dried. A level of lightening of up to 7 tones was obtained, while at the same time conserving a pleasant feel.

Comparative Example

Composition 1 was compared with Composition A described above for the oxidation dyeing example. After manufacture in an industrial tank, the two compositions were in the form of creams, the viscosities of which were measured at 25.0° C. for a shear rate of 70 s$^{-1}$ using an RS1 rotary rheometer (company ThermoFisher) equipped with a sanded-titanium geometry of cone-plate type (diameter 60 mm/angle 1°). After 25 minutes of shear stress, the viscosities thus measured were respectively 0.22 Pa·s for Composition 1 and 0.17 Pa·s for Composition A. After storage for two months at ambient temperature, Composition 1 showed an appearance and a viscosity that were comparable to the initial state (viscosity=0.27 Pa·s), whereas Composition A had a speckled appearance and a viscosity much lower than the initial state (viscosity=0.10 Pa·s). Observation of Composition A under an optical microscope with white light revealed the presence of bulk crystallites, the size of which was of the order of 100 μm. These crystallites resulted from the recrystallization of the cetylstearyl alcohol. After storage for two months at ambient temperature, the microscopic appearance of composition 1 was identical to the initial appearance.

What is claimed is:

1. A composition for treating keratin fibers, comprising, in a cosmetically acceptable medium:
    at least one oxidizing agent;
    at least one nonionic amphiphilic hydrophobic compound which is solid at ambient temperature chosen from steareth-2, steareth-3, steareth-4, steareth-5, steareth-6, ceteth-2, ceteth-3, ceteth-4, ceteth-5, ceteareth-2, ceteareth-3, ceteareth-4, ceteareth-5, beheneth-5, cocamide MEA, cocamide MIPA, cocamide DEA, stearamide MEA, stearamide DEA, myristamide DEA, myristamide MEA, polyglyceryl-2 distearate, polyglyceryl-3 distearate, polyglyceryl-2 stearate, polyglyceryl-3 stearate, peg-2 stearate, peg-3 stearate, peg-4 stearate, sorbitan distearate, sorbitan palmitate, sorbitan stearate, sorbitan tristearate, myristyl glucoside, cetearyl glucoside, and arachidyl glucoside; and
    at least one hydrophilic surfactant chosen from cationic and zwitterionic hydrophilic surfactants;
    wherein the at least one nonionic amphiphilic hydrophobic compound is present in an amount ranging from 2% to 30% by weight, relative to the total weight of the oxidizing composition;
    wherein the weight ratio of the at least one hydrophilic surfactant to the at least one nonionic amphiphilic hydrophobic compound ranges from 0.05:1 to 0.16:1;
    and further wherein the composition is in the form of an aqueous dispersion;
    with the proviso that the composition does not comprise hydrophilic surfactants other than cationic or zwitterionic hydrophilic surfactants.

2. A composition according to claim 1, wherein the at least one oxidizing agent is chosen from hydrogen peroxide, urea peroxide, alkali bromates, polythionates, and persalts.

3. A composition according to claim 1, wherein the at least one oxidizing agent is present in an amount ranging from 0.1% to 50% by weight, relative to the total weight of the oxidizing composition.

4. A composition according to claim 1, wherein the at least one nonionic amphiphilic hydrophobic compound comprises at least one $C_{12}$-$C_{30}$ saturated fatty chain linked, via an ether, ester, amide, or carbamate bond, to a polar head composed of at least one unit chosen from oxyalkylene units, sorbitan units, sugar units, and other polyol units.

5. A composition according to claim 1, wherein the at least one hydrophilic surfactant has a calculated HLB ranging from 10 to 50.

6. A composition according to claim 1, further comprising at least one $C_{12}$-$C_{30}$ fatty alcohol with a calculated HLB of less than 2.

7. A composition according to claim 6, in which the at least one $C_{12}$-$C_{30}$ fatty alcohol is chosen from linear and branched, saturated and unsaturated, non-(poly)oxyalkylenated and non-(poly)glycerolated alcohols comprising at least one fatty chain containing from 12 to 30 carbon atoms, the fatty chains being optionally substituted with one or two additional hydroxyl groups.

8. A composition according to claim 6, in which the at least one $C_{12}$-$C_{30}$ fatty alcohol is present in an amount ranging from 0 to 10% by weight, relative to the total weight of the oxidizing composition.

9. A composition according to claim 8, in which the at least one $C_{12}$-$C_{30}$ fatty alcohol is present in an amount of 0%.

10. A process for treating keratin fibers, comprising
    applying to the keratin fibers a composition for treating keratin fibers comprising, in a cosmetically acceptable medium:
        at least one oxidizing agent;
        at least one nonionic amphiphilic hydrophobic compound which is solid at ambient temperature chosen from steareth-2, steareth-3, steareth-4, steareth-5, steareth-6, ceteth-2, ceteth-3, ceteth-4, ceteth-5, ceteareth-2, ceteareth-3, ceteareth-4, ceteareth-5, beheneth-5, cocamide MEA, cocamide MIPA, cocamide DEA, stearamide MEA, stearamide DEA, myristamide DEA, myristamide MEA, polyglyceryl-2 distearate, polyglyceryl-3 distearate, polyglyceryl-2 stearate, polyglyceryl-3 stearate, peg-2 stearate, peg-3 stearate, peg-4 stearate, sorbitan distearate, sorbitan palmitate, sorbitan stearate, sorbitan tristearate, myristyl glucoside, cetearyl glucoside, and arachidyl glucoside; and
        at least one hydrophilic surfactant chosen from cationic and zwitterionic hydrophilic surfactants;
    wherein the at least one nonionic amphiphilic hydrophobic compound is present in an amount ranging from 2% to 30% by weight, relative to the total weight of the oxidizing composition;

wherein the weight ratio of the at least one hydrophilic surfactant to the at least one non ionic amphiphilic hydrophobic compound ranges from 0.05:1 to 0.16:1;

and further wherein the composition for treating keratin fibers is in the form of an aqueous dispersion;

with the proviso that the composition does not comprise hydrophilic surfactants other than cationic or zwitterionic hydrophilic surfactants.

11. A method for making a stable cosmetic composition for treating keratin fibers comprising:

introducing into a cosmetic composition for treating keratin fibers, a composition comprising in a cosmetically acceptable medium:

at least one oxidizing agent;

at least one nonionic amphiphilic hydrophobic compound which is solid at ambient temperature chosen from steareth-2, steareth-3, steareth-4, steareth-5, steareth-6, ceteth-2, ceteth-3, ceteth-4, ceteth-5, ceteareth-2, ceteareth-3, ceteareth-4, ceteareth-5, beheneth-5, cocamide MEA, cocamide MIPA, cocamide DEA, stearamide MEA, stearamide DEA, myristamide DEA, myristamide MEA, polyglyceryl-2 distearate, polyglyceryl-3 distearate, polyglyceryl-2 stearate, polyglyceryl-3 stearate, peg-2 stearate, peg-3 stearate, peg-4 stearate, sorbitan distearate, sorbitan palmitate, sorbitan stearate, sorbitan tristearate, myristyl glucoside, cetearyl glucoside, and arachidyl glucoside; and at least one hydrophilic surfactant chosen from cationic and zwitterionic hydrophilic surfactants;

wherein the at least one nonionic amphiphilic hydrophobic compound is present in an amount ranging from 2% to 30% by weight, relative to the total weight of the oxidizing composition;

wherein the weight ratio of the at least one hydrophilic surfactant to the at least one nonionic amphiphilic hydrophobic compound ranges from 0.05:1 to 0.16:1;

and further wherein the composition is in the form of an aqueous dispersion;

with the proviso that the composition does not comprise hydrophilic surfactants other than cationic or zwitterionic hydrophilic surfactants.

* * * * *